(12) United States Patent
Kuusela et al.

(10) Patent No.: US 10,661,096 B2
(45) Date of Patent: May 26, 2020

(54) THERAPEUTIC RADIATION TREATMENT

(71) Applicant: Varian Medical Systems International AG, Cham (CH)

(72) Inventors: Esa Kuusela, Espoo (FI); Janne I. Nord, Espoo (FI); Joakim Pyyry, Helsinki (FI); Perttu Niemelä, Espoo (FI)

(73) Assignee: Varian Medical Systems International AG, Steinhausen (CH)

( * ) Notice: Subject to any disclaimer, the term of this patent is extended or adjusted under 35 U.S.C. 154(b) by 198 days.

(21) Appl. No.: 15/662,853

(22) Filed: Jul. 28, 2017

(65) Prior Publication Data

US 2019/0030367 A1      Jan. 31, 2019

(51) Int. Cl.
*A61N 5/00*     (2006.01)
*A61N 5/10*     (2006.01)

(52) U.S. Cl.
CPC ........... *A61N 5/1031* (2013.01); *A61N 5/103* (2013.01); *A61N 2005/1041* (2013.01)

(58) Field of Classification Search
CPC ............................... A61N 5/103; A61N 5/1031
USPC .......................................................... 600/1–8
See application file for complete search history.

(56) References Cited

FOREIGN PATENT DOCUMENTS

| | | |
|---|---|---|
| EP | 2899659 A1 | 7/2015 |
| WO | 2011153639 A2 | 12/2011 |
| WO | 2016144914 A1 | 9/2016 |
| WO | 2017041194 A1 | 3/2017 |

OTHER PUBLICATIONS

PCT Search Report and Written Opinion from International Application No. PCT/EP2018/069715, dated Nov. 23, 2018; 13 pages.

*Primary Examiner* — John P Lacyk
(74) *Attorney, Agent, or Firm* — Fitch, Even, Tabin & Flannery LLP

(57) ABSTRACT

A control circuit uses a (possibly self-generated) seed radiation treatment plan to identify a portion (possibly only a point) of a multi-criteria optimization (MCO)-based Pareto surface. The control circuit then selects a sampling plan set for MCO planning by enlarging that portion of the Pareto surface region to thereby facilitate developing an optimized radiation treatment plan. A radiation treatment platform then uses that optimized radiation treatment plan to treat a patient by administering the radiation in accordance with the plan.

20 Claims, 2 Drawing Sheets

THERAPEUTIC RADIATION TREATMENT

TECHNICAL FIELD

These teachings relate generally to the therapeutic irradiation of a patient's target volume and more particularly to the use of radiation treatment plans in such regards.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted areas and adjacent healthy tissues, organs, or the like that are desired or even critical to continued survival of the patient. As a result, radiation is ordinarily applied in a carefully administered manner pursuant to a radiation treatment plan to at least attempt to restrict the radiation to a given target volume.

Many radiation treatment plans provide for exposing the target volume to radiation from a number of different directions. Arc therapy, for example, comprises one such approach. In such a case it often becomes useful or necessary to also adjust various mechanical components (such as, for example, multi-leaf collimators) of the treatment system when moving the radiation source with respect to the target volume. A radiation treatment plan therefore often provides information regarding useful or necessary adjustments to various mechanical components of the treatment system during such a treatment.

A radiation treatment plan typically comprises specified values for each of a variety of treatment-platform parameters during each of a plurality of sequential fields. Radiation treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting (sometimes referred to as incrementing) one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects.

Many prior art approaches employ multi-criteria optimization to develop a clinically worthy radiation treatment plan. The use of multi-criteria optimization, in turn, often involves use and investigation of a corresponding Pareto surface to identify and consider candidate radiation treatment plans. Unfortunately, a typical Pareto surface in such an application setting is relatively large as compared to the useful set of solutions. As a result, it can be very time consuming and/or consumptive of computational power to locate possibly useful plans using such an approach.

BRIEF DESCRIPTION OF THE DRAWINGS

The above needs are at least partially met through provision of the apparatus and approaches described in the following detailed description, particularly when studied in conjunction with the drawings, wherein.

Figure 1:
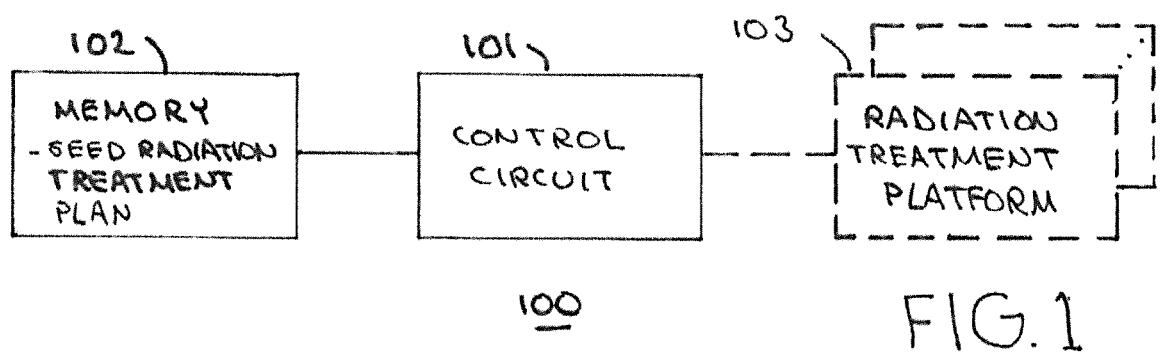
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments a control circuit couples to a memory having a seed radiation treatment plan stored therein. (By one approach the control circuit is configured to initially generate this seed radiation treatment plan, and if desired the seed radiation treatment plan constitutes a clinically relevant plan for a particular patient.) The control circuit uses the seed radiation treatment plan to identify a portion of a multi-criteria optimization (MCO)-based Pareto surface. The control circuit then selects a sampling plan set for MCO planning by enlarging that portion of the Pareto surface region to thereby facilitate developing an optimized radiation treatment plan. A radiation treatment platform then uses that optimized radiation treatment plan to treat a patient by administering the radiation in accordance with the plan.

By one approach the aforementioned identified portion of the MCO-based Pareto surface comprises a point on that surface. By one approach the control circuit enlarges the aforementioned portion by, at least in part, taking steps from the seed radiation treatment plan in different directions to thereby facilitate consideration of different sample radiation treatment plans that are nevertheless near to the seed radiation treatment plan (and hence more likely to be clinically relevant). By one approach these different sample radiation treatment plans are "near" the seed radiation treatment plan when one or more predetermined quality indexes are within at least one predetermined clinical goal and a tangent plane difference therebetween does not exceed a predetermined amount. This process could also utilize predetermined trade-off limits previously specified by the user.

By one approach the control circuit enlarges the aforementioned portion of the Pareto surface region by, at least in part, taking consecutive steps from the seed radiation treatment plan along a surface path from one sample radiation treatment plan to a next sample radiation treatment plan. If desired, the control circuit can use clinical information (regarding the patient and/or others) to define a direction of such an enlargement step to be made next. By one approach the control circuit uses at least one quadratic cost function having a varying weight matrix and object values to determine a desired direction and distance in which to enlarge the aforementioned portion.

Generally speaking, while prior art approaches often make use of the aforementioned Pareto surface, in fact such a surface in the context of candidate radiation treatment plans largely comprises regions that are of little interest or value. Accordingly, most plans based on most parts of such a surface have little or no therapeutic/clinical value or interest. Pursuant to the present teachings, however, many such areas can be avoided with confidence by beginning with a surface area likely to be of clinical interest and exploring other options within only a clinically-reasonable distance thereof.

These and other benefits may become clearer upon making a thorough review and study of the following detailed description. Referring now to the drawings, and in particular to FIG. 1, an illustrative apparatus 100 that is compatible with many of these teachings will now be presented.

For the sake of an illustrative example it will be presumed here that a control circuit 101 carries out some or all of the actions, steps, and/or functions described herein. Being a "circuit," the control circuit 101 comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

Amongst other things this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

In this illustrative example the memory 102 also stores at least one seed radiation treatment plan. By one approach this seed radiation treatment plan is a complete, previously-optimized (and possibly even previously used to administer therapeutic radiation to a patient) radiation treatment plan. These teachings will also accommodate, however, a seed that comprises a non-optimized radiation treatment plan if desired. Generally speaking, this seed radiation treatment plan is a clinically relevant plan for a particular patient of interest as described herein. As used herein, the expression "clinically relevant" means that the plan was designed to administer radiation in a manner that is consistent with one or more currently-available radiation treatment platforms, that the plan was designed to address a target volume in a patient that is also consistent with the aforementioned particular patient of interest, and that the plan has been approved by a clinician having corresponding authority in those regards.

In this example the control circuit 101 may also include, if desired, a network interface configured to provide a mechanism for the control circuit 101 to communicate with other elements (such as other memories, servers, radiation treatment platforms, and so forth). Network interfaces, including both wireless and non-wireless platforms, are well understood in the art and require no particular elaboration here.

Also if desired, and as illustrated in FIG. 1, this apparatus 100 can include one or more radiation treatment platforms 103. Generally speaking a radiation treatment platform comprises a radiation source that emits a beam and one or more beam-shaping components (such as multi-leaf collimators). A given radiation treatment platform may also include mechanisms to adjust the position of the radiation source with respect to the patient during the treatment process. There are numerous examples in these regards (such as Varian's Volumetric Arc Therapy (VMAT) and RapidArc® Radiotherapy-based systems) and the present teachings are not overly sensitive to any particular choices amongst these possibilities.

Figure 2:
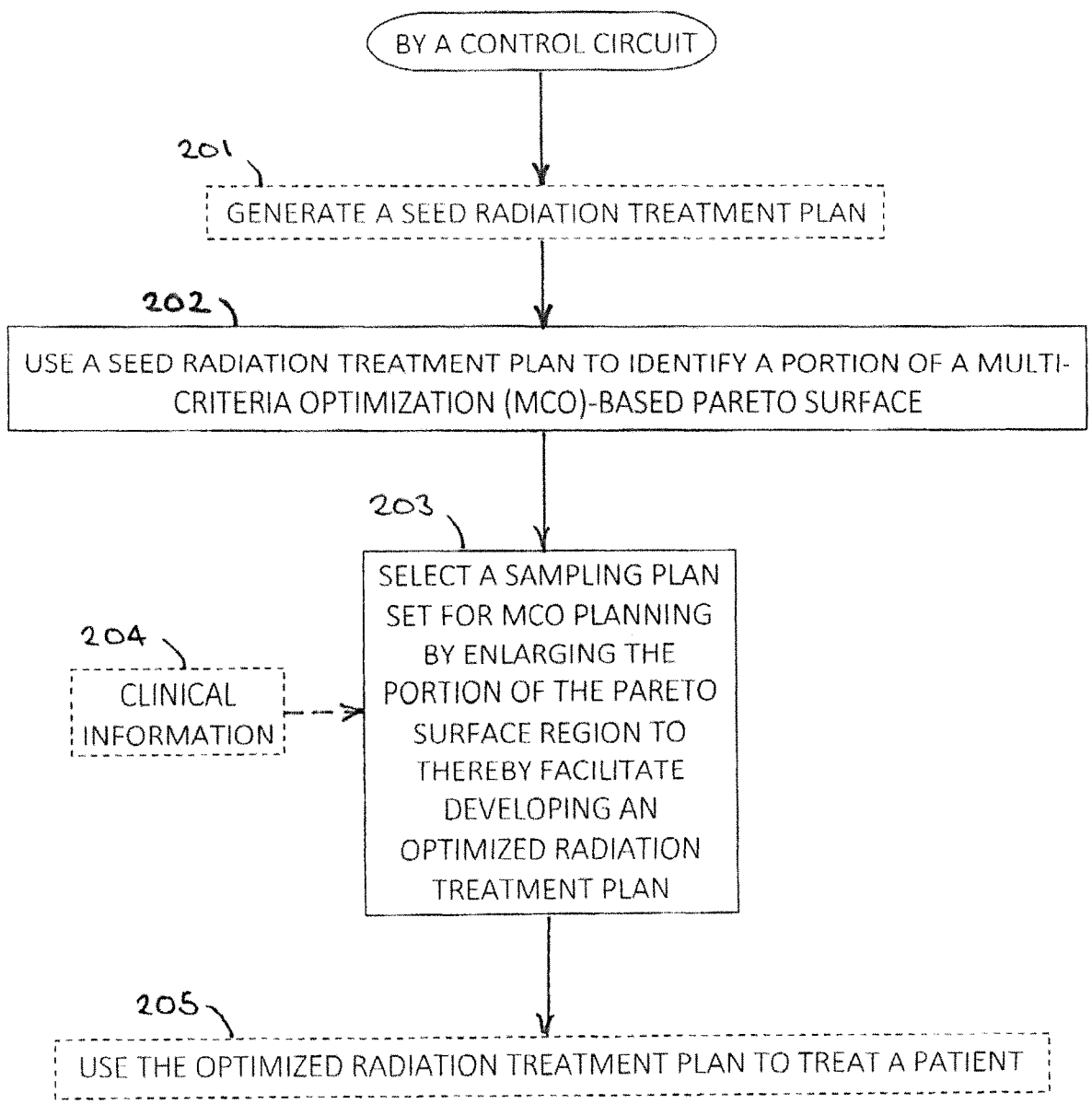
FIG. 2 comprises a flow diagram as configured in accordance with various embodiments of these teachings.

FIG. 2 presents a process 200 that can be carried out (in whole or in part) by the aforementioned control circuit 101.

By one optional approach, as illustrated at optional block 201, the control circuit 101 generates one or more of the aforementioned seed radiation treatment plans. This can comprise, for example, using an automated knowledge-based approach where a clinically relevant plan is generated by comparing the geometry of a current case into a set of existing plans made for different patients with different geometry. In a typical application setting the seed plan is created by applying rules that specify how patient geometry affects what was considered to be an optimal solution. These rules can be inferred, for example, from the set of existing plans.

Generation of a seed radiation treatment plan can itself be based on one or more previously-determined treatment plans if desired. By one approach, that seed plan can be manually generated with as much or as little detail as may be desired. The generated seed radiation treatment plan (or plans) can be stored in the aforementioned memory 102 pending usage.

In any event, at block 202 the control circuit 101 uses a seed radiation treatment plan (obtained, for example, from the aforementioned memory 102) to identify a portion of a multi-criteria optimization (MCO)-based Pareto surface. Multi-criteria optimization (also known as multi-objective optimization, multi-objective programming, vector optimization, multi-attribute optimization, or Pareto optimization) is an area of multiple-criteria decision making involving more than one objective function to be optimized simultaneously with respect to another. Multi-criteria optimization can provide useful results in an application setting where there are conflicting trade-offs between two or more objectives.

For a nontrivial multi-criteria optimization problem, there does not usually exist a single solution that simultaneously optimizes each objective. In that case, the objective functions can be said to be conflicting, and there exists a (possibly infinite) number of Pareto optimal solutions. Without additional subjective preference information, all Pareto optimal solutions may be considered equally good. The goal may be to find a representative set of Pareto optimal solutions and/or to quantify the trade-offs in satisfying the different objectives, and/or to find a single solution that satisfies the subjective preferences of a human decision maker.

In the context of developing a radiation treatment plan, and using intensity modulated radiation therapy (IMRT, including here also VMAT) as a concrete example, the desired radiation treatment plan is developed via an optimization process where the planner requests an optimal solution by defining a set of quality metrics $Q_i$ (such as target homogeneity, critical organ sparing, and so forth, where it may be later assumed that these quality metrics $Q_i$'s are defined so that a smaller numerical value is always preferred over a larger value) and specifying desired ratios or other relationships of the different quality metrics. In a traditional IMRT optimization process the planner may associate a desired goal value for each of the quality metrics ($q_i$) and define a relative priority (i.e., a weighting) ($w_i$) for each of these objectives. The optimization task can then be formulated, for example, by writing a quadratic cost function $C=\text{sum}(w_i(Q_i-q_i)^2)$. The desired plan can then be automatically generated by minimizing the cost function C.

Often, however, it is not easy to describe the optimal condition by just presenting the cost function. In particular, the optimal solution of such a cost function may not necessarily describe the clinically best balance between the quality metrics. Or, as another example, the dose distribution might have some undesired features that are difficult to present as a quality metric. Multi-criteria optimization approaches provide a powerful way to address such concerns.

These multi-criteria-optimization approaches include creating/defining a corresponding Pareto surface. In a not untypical prior art solution the plan generation is performed by first selecting a set of anchor plans that span the region on the Pareto surface and then creating more plans in this region until the shape of the Pareto surface is defined with sufficient accuracy everywhere inside the region spanned the anchor plans. After the sample plan set is constructed the user can navigate in the region spanned by the anchor plans.

It is, however, often difficult to estimate feasible anchor plan locations using that prior art approach. In particular, it is often the case that a major part of the region spanned by the anchor plans is clinically uninteresting. As a result, exploring/considering such areas can be a waste of computational resources and/or human attention and resources.

By using the seed radiation treatment plan as described above to identify a portion of an MCO-based Pareto surface, this process 200 starts from a known clinically-relevant plan (i.e., the seed radiation treatment plan) and uses that useful starting point to identify a corresponding portion of the MCO-based Pareto surface (i.e., that portion of the MCO-based Pareto surface that corresponds to the seed radiation treatment plan). By one approach the identified "portion" comprises a point on the MCO-based Pareto surface.

At block 203 this process 200 then provides for selecting a sampling plan set for MCO planning by enlarging the aforementioned portion of the Pareto surface region to thereby facilitate developing an optimized radiation treatment plan. These teachings are highly flexible in these regards and will accommodate a variety of practical approaches.

By one approach, for example, the control circuit 101 can use clinical information 204 (obtained, for example, from the aforementioned memory 102) to define a direction of an enlargement step to be made next when enlarging the aforementioned portion. Examples of clinical information that can be used to define the direction of the step include but are not limited to a known quality index goal value (as defined, for example, in a treatment protocol) that has not yet been reached and a TCP (tumor control probability) and/or NTCP (normal tissue complication probability) model that describes the importance of certain quality indices (as it can be useful to try a direction that provides a meaningful trade-off between two different complication probabilities).

As another example in these regards, the control circuit 101 can enlarge the aforementioned portion of the Pareto surface region, at least in part, by using at least one quadratic cost function having a varying weight matrix and object values to determine a desired direction and distance in which and by which to enlarge the aforementioned portion of the Pareto surface region.

Generally speaking, these teachings will accommodate enlarging the aforementioned portion of the Pareto surface region, at least in part, by taking steps from the seed radiation treatment plan in different directions on that surface to thereby facilitate consideration of different sample radiation treatment plans that are near the seed radiation treatment plan. (That which is "near" can be determined at the time of need by the user. As one useful example in these regards, a sample radiation treatment plan can be considered "near" to the seed radiation treatment plan when predetermined quality indexes are within at least one predetermined clinical goal of choice and tangent plane differences therebetween do not exceed a predetermined amount. Those skilled in the art will understand that the expression "tangent plane" refers to the tangent plane of the Pareto surface at the location of the seed plan and at least one of the corresponding sample plans.) This process 200 could also utilize acceptable trade-off limits previously established by the user.

As noted, enlarging the aforementioned portion of the Pareto surface region can comprise taking a step from the seed radiation treatment plan portion in one or more different directions. If desired, enlarging the aforementioned portion can also comprise, at least in part, taking consecutive steps from the seed radiation treatment plan along a surface path (i.e., along a path on the Pareto surface) from one sample radiation treatment plan to a next sample radiation treatment plan.

By one approach the searching can be performed either by always taking the next step from the seed plan in a different direction or by continuing and searching the next sample plan from the vicinity of the former sample. When the Pareto surface sampling is done using a continuous path the order in which directions are sampled can be determined as a function, at least in part, of quality metrics or related clinical goals. For example if some user-given clinical goal is not met in the seed plan, it could be beneficial to start the sample plan searching in a direction that improves the quality metric that best corresponds to that presently unmet goal.

This process 200 will accommodate searching the Pareto surface near the seed plan using a quadratic function of the quality metrics. For example, the full quadratic form can be parametrized as (Q−q)w(Q−q) where matrix w defines the weights of different quality indexes and the vector q defines the objective value for the quality metrics. If the seed plan was created with known (for example, diagonal) w and q, the new plan can be searched by perturbation of these values. Examples in these regards include:

The new q is moved towards the direction where the new optimal plan is desired to locate; and The new w is selected so that while the trade-off is within desired bounds a longer step is made but if the trade-offs start to be unacceptable the step is smaller in size.

At optional block 205 this process 200 will accommodate using the resultant optimized radiation treatment plan to treat a patient. This activity can require the use of an appropriate radiation treatment platform 102 as described above.

So configured, these teachings permit a Pareto surface-based multi criteria approach to be greatly streamlined by leveraging a useful seed plan to identify a part of the surface that is likely a useful part of the surface and then exploring the surface in the vicinity of that location for a better, more (or most) appropriate plan for a particular patient. Importantly, these teachings require less computational power and hence can reduce the hardware/software requirements typically utilized to achieve similar results using prior art approaches.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. An apparatus comprising:
    a memory having a seed radiation treatment plan stored therein wherein the seed radiation treatment plan comprises a radiation treatment plan designed to administer radiation in a manner consistent with at least one currently-available radiation treatment platform;
    a control circuit operably coupled to the memory and configured to:
        use the seed radiation treatment plan to identify a portion of a multi-criteria optimization (MCO)-based Pareto surface;
        select a sampling plan set for MCO planning by enlarging the portion of the Pareto surface region to thereby facilitate developing an optimized radiation treatment plan;
    a radiation treatment platform configured to use the optimized radiation treatment plan to treat a patient.

2. The apparatus of claim 1 wherein the seed radiation treatment plan comprises a clinically relevant plan for the patient.

3. The apparatus of claim 1 wherein the control circuit is further configured to:
    generate the seed radiation treatment plan;
    store the seed radiation treatment plan in the memory.

4. The apparatus of claim 3 wherein the control circuit is configured to generate the seed radiation treatment plan using an automated knowledge-based approach.

5. The apparatus of claim 1 wherein the portion of the multi-criteria optimization (MCO)-based Pareto surface comprises a point on the multi-criteria optimization (MCO)-based Pareto surface.

6. The apparatus of claim 1 wherein the control circuit is configured to enlarge the portion of the Pareto surface region by, at least in part, taking steps from the seed radiation treatment plan in different directions to thereby facilitate consideration of different sample radiation treatment plans that are near the seed radiation treatment plan.

7. The apparatus of claim 6 wherein the different sample radiation treatment plans are near to the seed radiation treatment plan when predetermined quality indexes are within at least one predetermined clinical goal and tangent plane differences therebetween do not exceed a predetermined amount.

8. The apparatus of claim 1 wherein the control circuit is configured to enlarge the portion of the Pareto surface region by, at least in part, taking consecutive steps from the seed radiation treatment plan along a surface path from one sample radiation treatment plan to a next sample radiation treatment plan.

9. The apparatus of claim 1 wherein the control circuit is configured to enlarge the portion of the Pareto surface region by, at least in part, using clinical information to define a direction of an enlargement step to be made next.

10. The apparatus of claim 1 wherein the control circuit is configured to enlarge the portion of the Pareto surface region by, at least in part, using at least one quadratic cost function having a varying weight matrix and object values to determine a desired direction and distance in which to enlarge the portion of the Pareto surface region.

11. A method comprising:
    by a control circuit:
        using a seed radiation treatment plan to identify a portion of a multi-criteria optimization (MCO)-based Pareto surface, wherein the seed radiation treatment plan comprises a radiation treatment plan designed to administer radiation in a manner consistent with at least one currently-available radiation treatment platform;
        selecting a sampling plan set for MCO planning by enlarging the portion of the Pareto surface region to thereby facilitate developing an optimized radiation treatment plan;
        using the optimized radiation treatment plan to treat a patient.

12. The method of claim 11 wherein the seed radiation treatment plan comprises a clinically relevant plan for the patient.

13. The method of claim 11 further comprising:
    generating the seed radiation treatment plan.

14. The method of claim 13 wherein generating the seed radiation treatment plan comprises using an automated knowledge-based approach.

15. The method of claim 11 wherein the portion of the multi-criteria optimization (MCO)-based Pareto surface comprises a point on the multi-criteria optimization (MCO)-based Pareto surface.

16. The method of claim 11 wherein enlarging the portion of the Pareto surface region comprises, at least in part, taking steps from the seed radiation treatment plan in different directions to thereby facilitate consideration of different sample radiation treatment plans that are near the seed radiation treatment plan.

17. The method of claim 16 wherein the different sample radiation treatment plans are considered near to the seed radiation treatment plan when predetermined quality indexes are within at least one predetermined clinical goal and tangent plane differences therebetween do not exceed a predetermined amount.

18. The method of claim 11 wherein enlarging the portion of the Pareto surface region comprises, at least in part, taking consecutive steps from the seed radiation treatment plan along a surface path from one sample radiation treatment plan to a next sample radiation treatment plan.

19. The method of claim 11 wherein enlarging the portion of the Pareto surface region comprises, at least in part, using clinical information to define a direction of an enlargement step to be made next.

20. The method of claim 11 wherein enlarging the portion of the Pareto surface region comprises, at least in part, using at least one quadratic cost function having a varying weight matrix and object values to determine a desired direction and distance in which to enlarge the portion of the Pareto surface region.

* * * * *